(12) United States Patent
Tavernelli et al.

(10) Patent No.: US 11,728,011 B2
(45) Date of Patent: Aug. 15, 2023

(54) SYSTEM AND METHOD FOR MOLECULAR DESIGN ON A QUANTUM COMPUTER

(71) Applicant: INTERNATIONAL BUSINESS MACHINES CORPORATION, Armonk, NY (US)

(72) Inventors: Ivano Tavernelli, Wädenswil (CH); Panagiotis Barkoutsos, Zurich (CH); Stefan Woerner, Zurich (CH); Alessandro Curioni, Gattikon (CH); Fotios Gkritsis, London (GB)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1110 days.

(21) Appl. No.: 16/397,281

(22) Filed: Apr. 29, 2019

(65) Prior Publication Data

US 2020/0342959 A1 Oct. 29, 2020

(51) Int. Cl.
| | |
|---|---|
| *G01N 33/48* | (2006.01) |
| *G01N 33/50* | (2006.01) |
| *G16C 10/00* | (2019.01) |
| *G06N 10/00* | (2022.01) |
| *G16C 20/50* | (2019.01) |

(52) U.S. Cl.
CPC ............ *G16C 10/00* (2019.02); *G06N 10/00* (2019.01); *G16C 20/50* (2019.02)

(58) Field of Classification Search
CPC ......... G16C 10/00; G16C 20/50; G06N 10/00
See application file for complete search history.

(56) References Cited

U.S. PATENT DOCUMENTS

| | | | |
|---|---|---|---|
| 5,854,992 A | 12/1998 | Shakhnovich et al. | |
| 6,772,073 B2 | 8/2004 | Freire et al. | |
| 8,849,580 B2 | 9/2014 | Kauffman et al. | |
| 2003/0216900 A1* | 11/2003 | Rosenthal | G16C 10/00 703/11 |
| 2005/0273306 A1 | 12/2005 | Hilton et al. | |
| 2012/0095743 A1* | 4/2012 | Flohil | G16B 15/00 703/11 |
| 2016/0321432 A1* | 11/2016 | Mondal | G16C 20/30 |

FOREIGN PATENT DOCUMENTS

WO 2005122052 A1 12/2005

OTHER PUBLICATIONS

Moll et al., "Quantum optimization using variational algorithms on near-term quantum devices", Quantum Science Technology, vol. 3, No. 3, Jun. 19, 2018, p. 030503.

O'Malley et al., "Scalable Quantum Simulation of Molecular Energies", Physical Review X, vol. 6, No. 3 Jul. 18, 2016, XP055462912.
Lu et al., "Quantum Chemistry Simulation on Qunatum Computers: Theories and Experiments", Physical Chemistry Chemical Physics, vol. 14, No. 26, Jan. 1, 2012, p. 9411, XP055724772.
PCT/EP2020/060429 International Search Report, dated Oct. 7, 2020.
PCT/EP2020/060429 Written Opinion, dated Oct. 7, 2020.
Cao et al. "Quantum Chemistry in the Age of Quantum Computing", rXiv:1812.09976v2 [quant-ph] Dec. 28, 2018.
Meng et al. "Computing Alchemical Free Energy Differences with Hamiltonian Replica Exchange Molecular Dynamics (H-REMD) Simulations", J. Chem Theory Comput. Sep. 13, 2011; 7(9): 2721-2727. doi:10.1021/ct200153u.
Reiher et al. "Elucidating Reaction Mechanisms on Quantum Computers", arXiv:1605.03590v2 [quant-ph] May 25, 2016.
Von Lilienfeld et al. "Variational Particle No. Approach for Rational Compound Design", PRL 95, 153002 (2005).
Wang et al. "Designing Molecules by Optimizing Potentials", J. Am. Chem. Soc. 2006, 128, pp. 3228-3232.
Wang et al. "A Generalised Variational Quantum Eigensolver", arXiv:1802.00171v2 [quant-ph] Jun. 25, 2018.
Kandala et al. "Hardware-efficient variational quantum eigensolver for small molecules and quantum magnets", Nature, vol. 549, Sep. 14, 2017, doi: 10.1038/nature 23879, pp. 242-246.
Harris et al. "Quantum-assisted biomolecular modelling", Phil Trans R. Soc. A, vol. 368, 2010, doi: 10.1098/rsta.2010.0087, pp. 3581-3592.
Pauca et al. "Automating the Development of Quantum Computational Software", Proceedings of the 47th ACM Southeast Conference, Mar. 2007, pp. 541-543.
Cao et al. "Potential of Quantum Computing for Drug Discovery", IBM journal of Research and Development, vol. 62, No. 6, Nov. 1, 2018, 20 pages.

* cited by examiner

*Primary Examiner* — Russell S Negin
(74) *Attorney, Agent, or Firm* — Amin, Turocy & Watson, LLP

(57) ABSTRACT

A method of designing a molecule for an environment of interest using a quantum computer includes providing a linear superposition of a plurality of molecular species, the plurality of molecular species being initially weighted by equal initial coefficients; determining a lowest-energy quantum state for the superposition of the plurality of molecular species in a vacuum environment and in the environment of interest using a quantum optimization process; calculating a difference in lowest energy states between the vacuum environment and the environment of interest for each molecular species to provide a cost of the superposition of the plurality of molecular species; performing a quantum optimization process to determine a minimum cost for the superposition of the plurality of molecular species and to determine updated coefficients weighting the plurality of molecular species; and identifying the molecule for the environment of interest based on a comparison of the updated coefficients.

18 Claims, 14 Drawing Sheets

SYSTEM AND METHOD FOR MOLECULAR DESIGN ON A QUANTUM COMPUTER

BACKGROUND

The currently claimed embodiments of the present invention relate to quantum computation, and more specifically, to a system and method for molecular design on a quantum computer.

Molecular design can allow simulation of an interaction between molecules or between molecules and atomic species. The simulation can be used to identify structures that are suitable for particular applications. For example, it may be worthwhile to identify a biological molecule that would interact with an enzyme most efficiently or to identify a molecule that would interact with a specific solvent or mixture of solvents, etc. This can have large applications not only in the pharmaceutical and biomolecular arenas but also in other fields such as materials sciences, etc. Every molecular configuration can be favorable for a certain environment while being unfavorable for another. The search of the right configuration for a specific environment can allow us to simulate applications of molecules in various solvent environments and when scaled up can be applied to the interaction of molecules within enzyme pockets, for example.

This approach cannot be implemented using a classical computer due to the number of possible combinations of atoms for a particular molecule as well as the position of each atom in a molecule relative to the molecular species in the environment. The computation simulation using a classical computer may be intensive and can be lengthy as classical computers, although becoming powerful every day, are limited in computational power due to their inherent configuration of using bits or zeros and ones.

SUMMARY

An aspect of the present invention is to provide a method of designing a molecule for an environment of interest using a quantum computer. The method includes providing a linear superposition of a plurality of molecular species, the plurality of molecular species in the linear superposition being initially weighted by equal initial coefficients; determining a lowest-energy quantum state for the superposition of the plurality of molecular species in a vacuum environment using a quantum optimization process on the quantum computer; and determining a lowest-energy quantum state for the superposition of the plurality of molecular species in the environment of interest using the quantum optimization process on the quantum computer. The method further comprises calculating a difference in lowest energy states between the vacuum environment and the environment of interest for each molecular species of the plurality of molecular species to provide a cost of the superposition of the plurality of molecular species; performing a quantum optimization process on the quantum computer to determine a minimum cost for the superposition of the plurality of molecular species and determine updated coefficients weighting the plurality of molecular species; and identifying the molecule for the environment of interest based on a comparison of the updated coefficients.

In an embodiment, the identifying of the molecule includes identifying the molecule for the environment of interest having, atom-by-atom, the greatest coefficient in the updated coefficients, at each atomic position. In an embodiment, determining the lowest-energy quantum state for the superposition of the plurality of molecular species in the vacuum and in the environment of interest comprises using a Variational Quantum Eigensolver (VQE) method with a mapping of corresponding atomic orbital wavefunctions to qubits in the quantum computer. In an embodiment, performing the quantum optimization process on the quantum computer to determine the updated coefficients weighting the plurality of molecular species includes using a Variational Quantum Eigensolver (VQE) method. In an embodiment, determining the lowest-energy quantum state for the superposition of the plurality of molecular species in the environment of interest includes selecting a plurality of locations of each of the superposition of the plurality of molecular species in the environment of interest.

In an embodiment, the method further includes providing a representation of the environment of interest on the quantum computer to simulate a physical environment of interest. In an embodiment, providing the representation of the environment of interest comprises simulating the environment using electric charges placed at appropriate positions relative to each of the plurality of molecular species.

Another aspect of the present invention is to provide a quantum computer system to design a molecule for an environment of interest. The quantum computer system is configured to: receive as input a linear superposition of a plurality of molecular species, the plurality of molecular species in the linear superposition being initially weighted by equal initial coefficients; determine a lowest-energy quantum state for the superposition of the plurality of molecular species in a vacuum environment using a quantum optimization process; determine a lowest-energy quantum state for the superposition of the plurality of molecular species in the environment of interest using the quantum optimization process; calculate a difference in lowest energy states between the vacuum environment and the environment of interest for each molecular species of the plurality of molecular species to provide a cost of the superposition of the plurality of molecular species; perform a quantum optimization process on the quantum computer to determine a minimum cost for the superposition of the plurality of molecular species and determine updated coefficients weighting the plurality of molecular species; and identify the molecule for the environment of interest based on a comparison of the updated coefficients.

Yet another aspect of the present invention is to provide a non-transitory computer readable medium on which is stored a program, which when executed by a quantum computer causes the quantum computer to: receive as input a linear superposition of a plurality of molecular species, the plurality of molecular species in the linear superposition being initially weighted by equal initial coefficients; determine a lowest-energy quantum state for the superposition of the plurality of molecular species in a vacuum environment using a quantum optimization process; determine a lowest-energy quantum state for the superposition of the plurality of molecular species in the environment of interest using the quantum optimization process; calculate a difference in lowest energy states between the vacuum environment and the environment of interest for each molecular species of the plurality of molecular species to provide a cost of the superposition of the plurality of molecular species; perform a quantum optimization process on the quantum computer to determine a minimum cost for the superposition of the plurality of molecular species and determine updated coefficients weighting the plurality of molecular species; and identify the molecule for the environment of interest based on a comparison of the updated coefficients.

BRIEF DESCRIPTION OF THE DRAWINGS

The present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION

Figure 1:
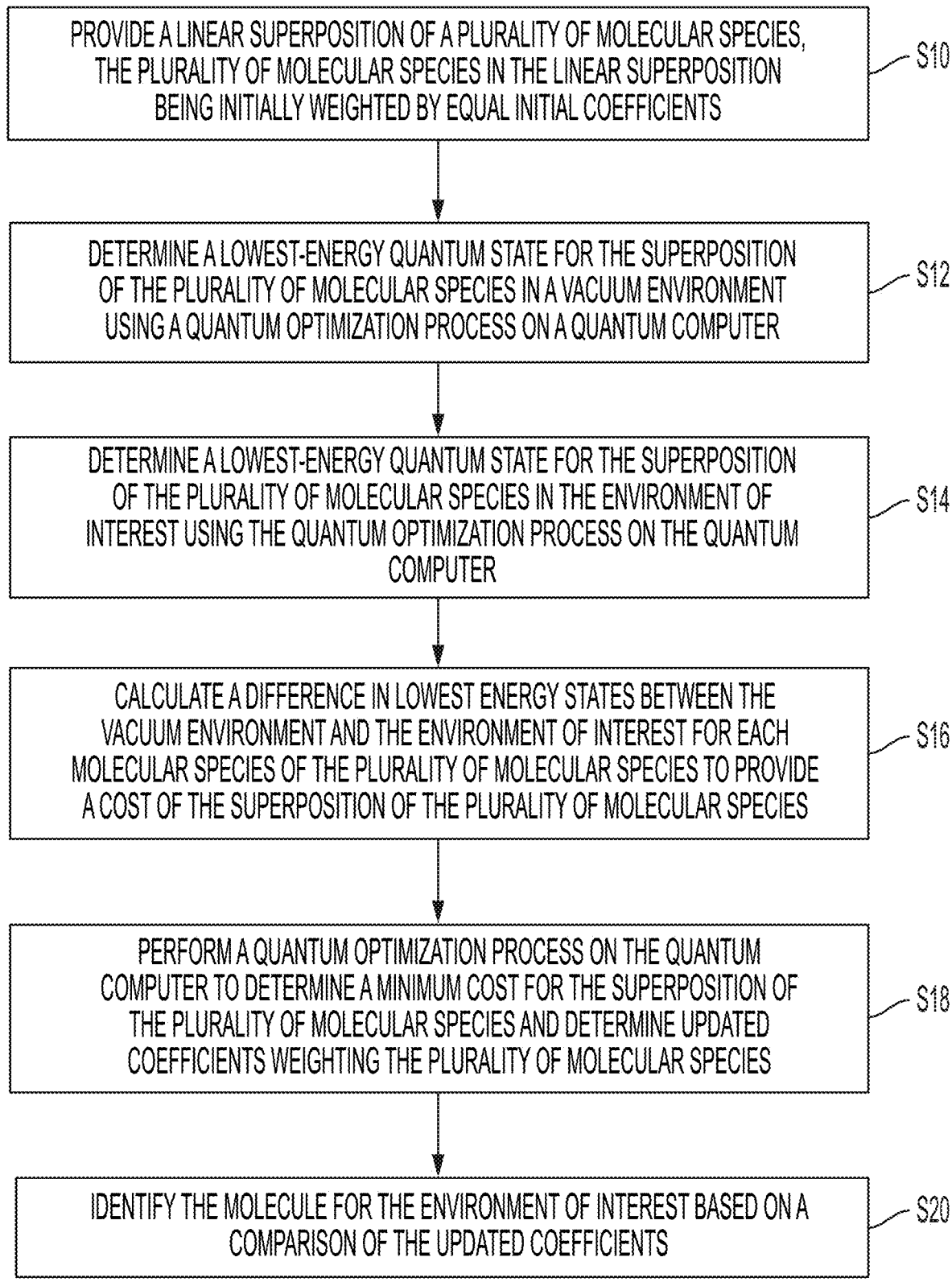
FIG. 1 is a flow diagram of a method of designing a molecule for an environment of interest using a quantum computer, according to an embodiment of the present invention.

FIG. 1 is a flow diagram of a method of designing a molecule for an environment of interest using a quantum computer, according to an embodiment of the present invention. The method includes providing a linear superposition of a plurality of molecular species, the plurality of molecular species in the linear superposition being initially weighted by equal initial coefficients, at S10. For example, as will be described further in detail in the following paragraphs, a set of candidate molecules can be selected, e.g. AB, BA, BC, CB, AC, CA, where A, B and C are selected possible atoms, such as H, Li, Na, etc. The selected linear superposition of molecules are initially weighted by equal initial weights or probability coefficients. This means that initially all molecules have equal chance of being selected as a molecule of choice for the environment of interest. Although diatomic molecules are used herein as an example, as it must be appreciated the present method is not limited to diatomic molecules but can include triatomic, or generally multi-atomic molecules such as polymers, peptides, proteins, etc.

The method further includes determining a lowest-energy quantum state for the superposition of the plurality of molecular species in a vacuum environment using a quantum optimization process on the quantum computer, at S12. The method also includes determining of the lowest-energy quantum state for the superposition of the plurality of molecular species in the environment of interest on the quantum computer, at S14. In an embodiment, the determining of the lowest-energy quantum state for the superposition of the plurality of molecular species in the vacuum and in the environment of interest includes using a Variational Quantum Eigensolver (VQE) method with a mapping of corresponding atomic orbital wavefunctions to qubits in the quantum computer. The use of the Variational Quantum Eigensolver (VQE) method along with the mapping method to map atomic orbital wavefunctions to qubits in the quantum computer will be explained further in detail in the following paragraphs. In an embodiment, determining of the lowest-energy quantum state for the superposition of the plurality of molecular species in the environment of interest can include selecting a plurality of locations of each of the superposition of the plurality of molecular species in the environment of interest. For example, specific atoms of the molecular superposition can be positioned at selected positions relative to species (atoms, ions, etc.) in the environment of interest or electric charges in the environment of interest.

The method also includes calculating a difference in lowest energy states between the vacuum environment and the environment of interest for each molecular species of the plurality of molecular species to provide a cost of the superposition of the plurality of molecular species, at S16. The method further includes performing a quantum optimization process on the quantum computer to determine a minimum cost for the superposition of the plurality of molecular species and determine updated coefficients weighting the plurality of molecular species, at S18. In an embodiment, performing the quantum optimization process on the quantum computer to determine the updated coefficients weighting the plurality of molecular species includes using a Variational Quantum Eigensolver (VQE) method.

The method further includes identifying the molecule for the environment of interest based on a comparison of the updated coefficients, at S20. In an embodiment, the identifying of the molecule includes identifying the molecule for the environment of interest having, atom-by-atom, the greatest coefficient (i.e., the weight at each atomic position) in the updated coefficients.

In an embodiment, the method may further include providing a representation of the environment of interest on the quantum computer to simulate a physical environment of interest. In an embodiment, providing the representation of the environment of interest comprises simulating the environment using electric charges placed at appropriate positions relative to each of the plurality of molecular species.

The term "environment of interest" is used herein to broadly mean any medium that is not part of a molecule under investigation. The "environment" can be for example, a solvent, an enzyme, or more generally a different molecular specie or atomic specie than the molecule under investigation. The "environment" can be a gas, a liquid, a solid, or any combination thereof.

The present method implemented on a quantum computer can overcome inherent limitations in a classical computer. In the present method, the evaluation of the required energy for the interaction in between one or more molecules and the external environment can be efficiently evaluated and the best configuration for every case can be found.

The present method can enable, for example, designing the best molecule (e.g., a drug) that can optimally bind (e.g., dock) in a given environment having an external potential (e.g., an enzyme pocket, for example). In an embodiment, the external potential can be simulated classically using point charges models, e.g., a molecular-mechanics (MM) description.

In classic computers, we are limited by (i) the cost of the evaluation of the molecular energy (solution of the electronic Schrodinger equation) and (ii), more importantly, by the costs associated to the search of new molecules in the exponentially large "chemical compound space," which is an NP-complete combinatorial optimization problem.

Therefore, we apply a Variational Quantum Eigensolver (VQE) algorithm that can simultaneously optimize the electronic structure and the atomic composition of a given molecular scaffold (e.g., the skeleton of a drug molecule). This can provide benefits from (i) the exponential seed up for the optimization of the electronic structure, and (ii) from the speed up for the search in the exponentially large (or better, combinatorial large) chemical compound space using quantum search and optimization algorithms.

As it must be appreciated from the above paragraphs, in an embodiment, the method allows for the performance of "alchemical" changes by substituting atoms characterized by their corresponding Effective Core Potentials (ECPs) in electronic structure problems, where the interaction between core and valence electrons is represented with the use of the Effective Core Potentials (ECPs). This enables the study of "alchemical" changes in a quantum computer, where the exponential scaling can be exploited for the search of different configurations.

An initial step is to perform only iso-electronic changes, i.e., without changes in the number of electrons, $N_e$. The next step is the relaxation of this constraint to enable the determination of the "optimal" solution regardless of the initial number of electrons.

In other words, in an embodiment, the method optimizes both electronic structure and nuclear composition to get the best fit with the external potential (the environment of interest). The cost function to be minimized is the energy difference between the molecule in vacuum and the molecule in the external potential or in the environment of interest. This energy can be referred to as the "binding energy." The binding energy is a measure of the molecular affinity for the given external potential (binding pocket) or environment of interest. The binding energy E(binding) is equal to a difference between the energy E(molecule in vacuum) and energy E(molecule in the external potential or environment of interest).

In an embodiment, the atomic composition of the molecule and its corresponding energy is optimized so that the binding energy is as large as possible. To compute the energy we need to define a Hamiltonian (the alchemical Hamiltonian) that depends on the nature of the nuclei and on the number of electrons. The function that describes the Alchemical Hamiltonian of the system can be expressed by Equation (1).

$$H(R, \{\alpha\}) = \sum_{I=1}^{N_n} \sum_{s_I=1}^{N_I^{max}} \alpha_{s_I}^I \left( \sum_{i=1}^{N_e} -\frac{1}{m_e} \nabla_{r_i}^2 - \frac{\tilde{Z}_I^{s_I}}{|r_i - R_I|} + v_{ECP}^{I,s_I}(|r_i - R_I|) \right) + \sum_{J<I} \frac{Z_I Z_J}{|R_I - R_J|} + V_{ee} \quad (1)$$

where:

$$V_{ee} = \sum_{i<j}^{N_e,N_e} \frac{e^2}{|r_i - r_j|}$$

is the electron-electron interaction;
- s: runs over the different chemical species allowed at each different atomic position (labelled with I);
- $\alpha_s^I$: are alchemical weights, with the constraint $\sum_s \alpha_{s_I}^I = 1 \forall I$;
- I, J: are indices over the different atoms in the system;
- $v_{ECP}^{I,s}$: is the potential generated by the core electrons of atom I in its alchemical form a;
- i, j: are indices over the electrons;
- $m_e$: is the mass of an electron;
- $Z_I$: is the atomic number of atom I;
- $\tilde{Z}_I$: are the valence charges defined by equation (2):

$$\tilde{Z}_I = Z_I - Z_e^{ECP} \quad (2)$$

and $N_e^{ECP}$ are the number of electrons in the core.

$N_I^{max}$: is a maximum number of replacements at atom I.

The NN-term interaction in Equation (1) is given by Equation (3):

$$\sum_{I<J} \frac{Z_I Z_J}{|R_I - R_J|} = \sum_{I<J} \frac{\tilde{Z}_I \tilde{Z}_J}{|R_I - R_J|} + \sum_{I<J} Z(R_I) v_{ECP}^J(R_I) \quad (3)$$

In an embodiment, the method optimizes (e.g., minimizes) the interaction of the system with a given external potential. Hence, the cost function C which is the energy difference between the molecule in vacuum and the molecule in the external potential or in the environment of interest can be minimized for a given environment or external potential. The cost function C can be expressed using the following Equation (4).

$$C = \beta_1 \int \rho_e(r) V_{potential}^\alpha(r) dr + \beta_2 E_{molecule} \quad (4)$$

where $\beta_1 + \beta_2 = 1$ and where $V_{potential}^\alpha(r)$ describes the external potential (environment). Where $\beta_1$ and $\beta_2$ are weight coefficients that weigh the interaction of a given molecule with the environment and the energy of the molecule, respectively. The term $p_e(r)$ corresponds to the density matrix of the molecule in the environment of interest. The density matrix is determined using the wavefunction of the system. The wavefunction of the system is calculated using the Variational Quantum Eigensolver (VQE) which will be explained further in the following paragraphs.

In order to determine the minimum in the cost function, the wavefunction of the alchemical mixture, i.e., the molecule with the environment as whole, is optimized. That is, the wavefunction for the alchemical mixture of elements at each atomic position measured by the alchemical weights $\{\alpha_s^I\}$ (included in the Hamiltonian in equation (1)) is optimized using the VQE by applying the following Equation (5) and thus determining the minimum energy E of the system.

$$H(R,\{\alpha\}) \xrightarrow{VQE} |\psi_0\rangle, E_0 \quad (5)$$

In addition, the alchemical weights or coefficients $\{\alpha_s^I\}$ are also optimized using VQE and the cost function in Equation (4). Due to the quantum nature of the method, the output of the quantum computer would provide a probabilistic answer. However, we need to converge to a solution to a limit that it is a unique species per atom, in order for the answer to be reconstructable in real-world conditions. The alchemical weights or coefficients are associated with corresponding molecular species in the superposition of the plurality of molecular species. Each alchemical weight or coefficient represents a probability of a corresponding molecular specie.

In an embodiment, it can be useful to represent the system in an atomic orbital basis. The calculated cost function represents a minimization over the subtraction between a variety of chemical compounds or molecules in vacuum and the interaction of the same chemical compounds or molecules within an environment of interest. The minimization of the cost function C or min(C) can be expressed using the following Equation (6).

$$\min(C) = \min\left[\sum_i^m c_i(\langle\psi|H_i^{env}|\psi\rangle - \langle\psi|H_i^{vacuum}|\psi\rangle)\right] \quad (6)$$

where $H^{vacuum}$ is the Hamiltonian of the molecule in vacuum (i.e., without the environment) and $H^{env}$ is the Hamiltonian of the molecule within the environment. The Hamiltonian in vacuum $H^{vacuum}$ can be derived initially as an even distribution of weights or coefficients between the Hamiltonians of all possible compounds designated by the pool of elements provided, as described in the method at S10 in FIG. 1. The Hamiltonian in vacuum can therefore be expressed by Equation (7).

$$H_{total}^{vacuum} = c_1 H_1^{vacuum} + c_2 H_2^{vacuum} + \ldots + c_m H_m^{vacuum} \quad (7)$$

$$H_{total}^{vacuum} = \sum_i^m c_m H_m^{vacuum}$$

The Hamiltonian that describes the interaction between the compound and the environment can be expressed by Equation (8).

$$H_{total}^{env} = c_1 H_1^{env} + c_2 H_2^{env} + \ldots + c_m H_m^{env} \quad (8)$$

$$H_{total}^{env} = \sum_i^m c_m H_m^{env}$$

In a more comprehensive manner, the Hamiltonians can be described by one-body terms and two-body terms. While performing the swap from vacuum to environment regime, the two body terms $g_{\alpha,\beta,\gamma,\delta}$ remain unchanged by the swapping, while the one body terms change, from $h_{\alpha,\beta} \to h'_{\alpha,\beta}$, where $\alpha$ and $\beta$ span over all the possible element combinations. The full construction of the Hamiltonian using one and two electron integrals can be expressed by Equation ($^9$).

$$H = h_{\mu,\nu} a_\mu^\dagger a_\nu + g_{\mu\nu\kappa\lambda} a_\mu^\dagger a_\nu^\dagger a_\kappa a_\lambda \quad (9)$$

The single-body terms are the only terms that transform when performing the alchemical change, since we are working on an atomic orbital basis. More specifically, the change of $h_{\alpha\beta}$ can be expressed by Equation (10).

$$h_{\mu\nu} = \sum_I \int dr \frac{[\phi_\mu(r)\phi_\nu(r)]Z_I}{|R_I^A - r|} + \sum_J \int \frac{[\phi_\mu(r)\phi_\nu(r)]C_J}{|R_J^C - r|} \quad (10)$$

where in the above formula the indexes used in the formula are denoting:

I: denotes summation on all the positions of the compound available for substitution;
J: denotes summation on all the positions of the charges situated around the compound;
Index A: shows the reference to the atoms;
Index C: shows the reference to the charges;
μ: denotes one of the possible positions in the compound, one part of the interacting pair;
ν: denotes another of the possible positions in the compound, the other part of the interacting pair;
$Z_I$: refers to atomic numbers; and
$C_J$: refers to the external charges.

Therefore, the coefficient $h_{\mu\nu}$ that represents the whole of the system can be expressed as Equation (11).

$$h_{\mu\nu} = \sum_I c_I h_{\mu\nu}^I \quad (11)$$

where, the index I corresponds to all the positions of the compound available for substitution, μ denotes one of the possible positions in the compound, one part of the interacting pair; and ν denotes another of the possible positions in the compound, the other part of the interacting pair. That holds true for a specific compound (denoted with μ, ν), regardless of its presence in an external field.

In an embodiment, it may be convenient, in order to minimize the execution time of the algorithm, to construct and operate on a single Hamiltonian, since we are only interested in their difference, as expressed in Equation (11).

$$\sum_I c_I h_{\mu\nu}^{env} - \sum_I c_I h_{\mu\nu}^v = \sum_I c_I (h_{\mu\nu}^{env} - h_{\mu\nu}^v) \quad (12)$$

The Hamiltonians that derive from one and two body integrals are expressed by the following Equations (13) and (14), respectively, in vacuum and in the environment of interest.

$$\hat{H}^v = h_{\mu\nu}^v \alpha_\mu^\dagger \alpha_\nu + g_{\mu\nu\kappa\lambda}^v \alpha_\mu^\dagger \alpha_\nu^\dagger \alpha_\kappa \alpha_\lambda \quad (13)$$

$$\hat{H}^{env} = h_{\mu\nu}^{env} \alpha_\mu^\dagger \alpha_\nu + g_{\mu\nu\kappa\lambda}^{env} \alpha_\mu^\dagger \alpha_\nu^\dagger \alpha_{78} \alpha_{80} \quad (14)$$

Since $g_{\mu\nu\kappa\lambda}^{env}$ in an environment is equal to $g_{\mu\nu\kappa\lambda}^v$ in vacuum because the two-body term does not change, Equation (12) can be simplified to a cost function that can be expressed by Equation (15).

$$C = \hat{H}^{env} - \hat{H}^v = \sum_I c_I (h_{\mu\nu}^{env} - h_{\mu\nu}^v) \alpha_\mu^\dagger \alpha_\nu \quad (15)$$

In an embodiment, a simple model can be implemented for understanding and having a more clear perspective on the combinations possible that derive from the pool of allotted elements and their behavior in a specific environment (e.g., one or more external potentials). For example, the model may include a three-dimensional system with a pair of charges on each axes and the desired "compound" at the center of those axes. As the compound is defined, the chemical combination of elements can be searched and the chemical combination that behave the best (i.e. have the lowest energy ground state to be as stable as possible) in that specific electric environment as defined by ambient charges and control charges can be found.

In an embodiment, a system is designed so that the system makes full use of the atomic orbitals scaling, instead of molecular scaling. For example, if N is the number of possible options for each position in the compound and K the number of positions of the compound itself, using molecular orbitals, the exponential scaling would be $N^K$. In the present implementation, the system exhibits a scaling of $$\frac{K(K-1)}{2} N^2,$$

taking advantage of the interactions as pairs of two and not as an ensemble spanning over the combination of the number of positions. In addition, the atomic orbitals exhibit symmetry that allows the construction of "symmetric" molecules (e.g., HLi and LiH). This allows reducing even further of the amount of molecule combination pairs required for construction.

In an embodiment, the system is modeled using a Gaussian. Each candidate molecule is modeled and then the output of the calculation serves as a basis for extracting the coefficients of the one-body integrals, as well as the two-body integrals. The Hamiltonian of each candidate molecule is then constructed, in respect to the environment of interest, using the difference of the one body terms in the environment and in vacuum. However, use of symmetry is made in order to simplify the system.

Figure 2:
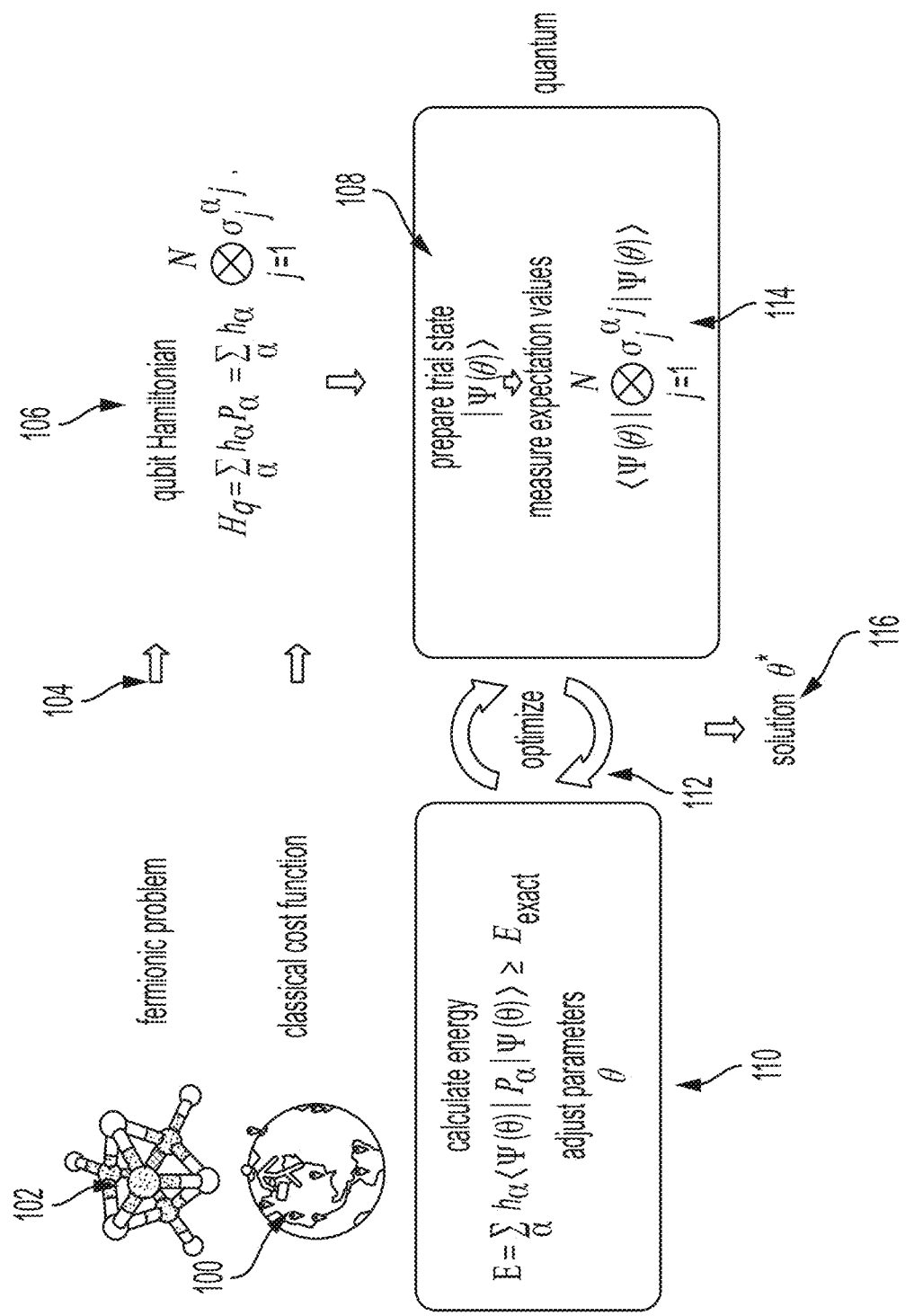
FIG. 2 is a schematic diagram showing a process for calculating the energy of a molecule and performing the optimization using the cost function and the wavefunction representing molecular system in the environment, according to an embodiment of the present invention.

FIG. 2 is a schematic diagram showing a process for calculating the energy of a molecule and performing the optimization using the cost function and the wavefunction representing molecular system in the environment, according to an embodiment of the present invention. As shown in FIG. 2, the cost function 100 is input into the quantum computer. However, because the qubits in the quantum computer obey boson statistics whereas electrons in an atom or molecule obey fermionic statistics 102, a transformation 104 from the fermionic space 104 into the bosonic space 106 is performed on the single-body integral coefficients of the Hamiltonian using the Jordan-Wigner transformation. The bosonic qubit Hamiltonian 106 for a candidate molecule is then constructed using a product of the coefficients in the bosonic space. Trial wavefunctions 108 are prepared and input into the quantum computer in a form of a series of qubits representing the atomic orbitals, as will explained further in detail in the following paragraphs. The atomic orbitals are mapped to the qubits. The atomic orbitals are mapped to one or more of the available qubits in the quantum computer.

In an embodiment, if the number of qubits is equal to the number of atomic orbitals no transformation is required on the Hamiltonian. However, if the number of qubits available is greater than the number of atomic orbitals needed for accurate modeling, then there would be a surplus in size of qubits in the circuit. In this case, the space (or matrix) of the Hamiltonian is padded with zeros to match the shape of the circuit, i.e., the number of available qubits, so as to maintain the same physical properties corresponding to the eigenvalues. If, on the other hand, the number of qubits available is less than the number of atomic orbitals needed for accurate modeling and thus the number of qubits is not sufficient for accurate modeling, then the atomic orbitals that would correspond to a higher number of qubits are discarded. In this way, matrices describing the Hamiltonian can be made with equal rank to the circuit.

To perform the quantum computation, a circuit is constructed to search the chemical space giving the thetas θ for the trial state used for the expected value their degrees of freedom, including the amount of precision desirable via the selection on the number of qubits.

Figure 3:
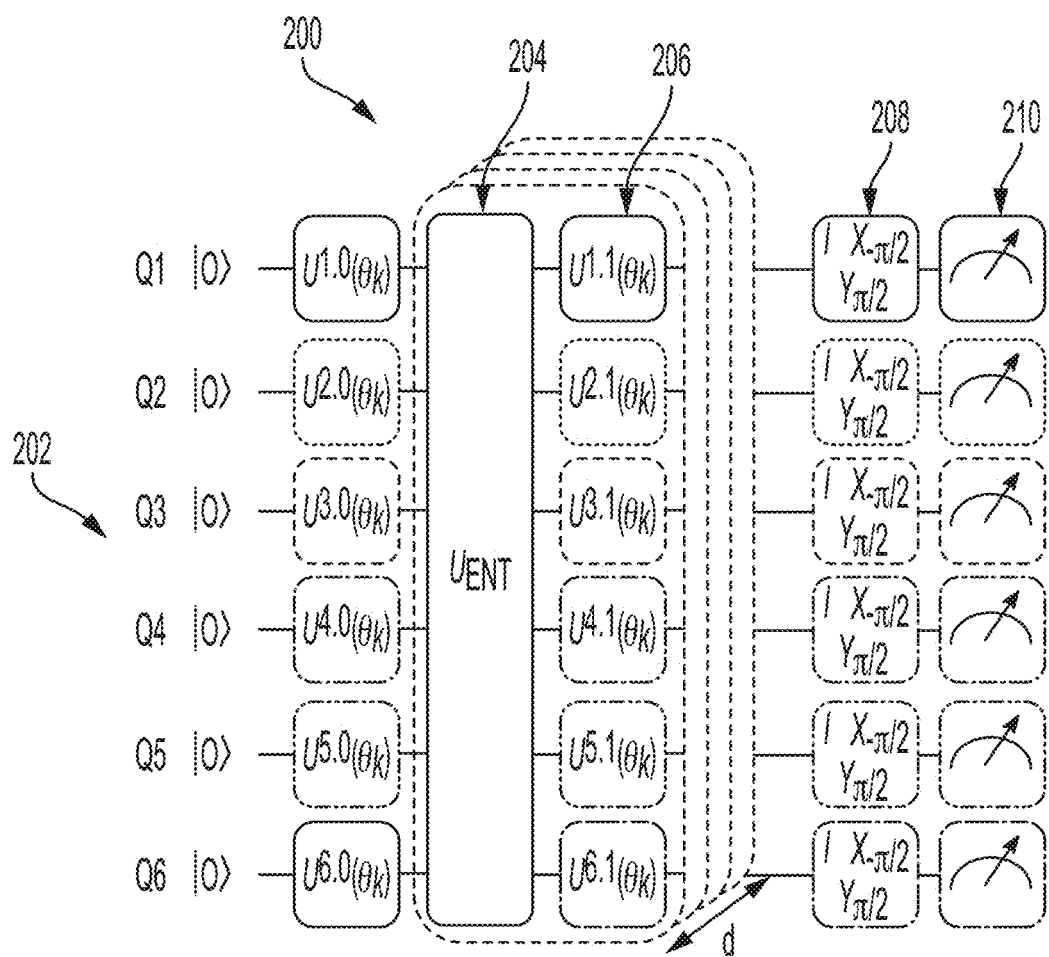
FIG. 3 shows an example of a quantum computer circuit using a plurality of qubits for trial-state preparation and energy estimation using a Variational Quantum Eigensolver (VQE), according to an embodiment of the present invention.

FIG. 3 shows an example of a quantum computer circuit 200 using a plurality of qubits for trial-state preparation and energy estimation using a Variational Quantum Eigensolver (VQE), according to an embodiment of the present invention. The quantum circuit 200 has a plurality of qubits 202 ($Q_1$, $Q_2$, . . . , $Q_6$). Although there are six qubits in this example, the general concepts of the current invention are not limited to any particular number of qubits. There could be more than, or less than six qubits in other embodiments. The qubits 202 are entangled using entangling unitary operator UENT "the entangler" 204 of the quantum circuit 200. Qubit rotations are performed on the entangled qubits using rotation operator $U_{q,d}(\theta_k)$ 206, where $\theta_k$ represent the Euler angles for each qubit q in the Block sphere, q identifies the qubit and i=0, 1, . . . , d refers to the depth position in the circuit 200. Qubit rotations can be implemented as a combination of Z and X gates, for example. However, other types of rotations can also be implemented depending on the configuration selected.

A set of post-rotations (I, $X_{-\pi/2}$ or $Y_{\pi/2}$) 208 are performed on the rotated entangled qubits. The qubits are then read out using measurement gates 210. The read out qubits are used to measure the expectation values of the individual Pauli terms in the Hamiltonian and to estimate the energy of the trial state. The Hamiltonian of each candidate compound/ molecule multiplied by a corresponding weight describes the probability of participation in the final compound/molecule. The depth "d" of the circuit represents the amount of gate operations needed to be executed in the quantum computer.

In an embodiment, the entangler $U_{ENT}$ 204 employed in the circuit 200 is one with all-to-all connectivity which can be implemented with, for example, CNOT gates. The use of a CNOT gate entangler provides the ability to access and search the total of Hilbert space made available by the dimensions of the problem. The initial trial state may not be important as each one of its qubits is subjected to $R_Y$ rotations upon optimization by the Variational Quantum Eigensolver (VQE). Although a CNOT gate is described herein as being used as an entangler operator, other types of gates can also be used for performing the entanglement operation.

As shown in FIG. 2, the Hamiltonian of each molecule is allowed to operate on the quantum object we created as a circuit, as shown at 110. That is, the Hamiltonian is allowed to operate on each sets of qubits representing the wavefunction to compute the ground state or minimum energy of that molecule, using the VQE method. In an embodiment, the value of the Euler angle θ is adjusted to change the state of the qubit and thus search for the minimum energy in the molecule in the environment. In an embodiment, an optimizer method 112 is used, for example by using the L-BFGS-B optimizer, to optimize the Euler angle θ used. L-BFGS is a limited memory algorithm based on the Broyden-Fletcher-Goldfarb-Shanno (BFGS) algorithm. It is a conventional algorithm for parameter estimation in machine learning. BFGS-B is a variant that handles simple box constraints.

After a set number of iterations, the optimizer method 112 returns an optimized state for optimization over the weights of each Hamiltonian by employing the Sequential Least Squares Programming (SLSQP) optimizer, since it specializes on optimizing scalar parameters, such as coefficients in question. SLSQP is a sequential least squares algorithm which uses the Han-Powell quasi-Newton method with a BFGS update of the B-matrix and an L1-test function in the step length algorithm. The optimizer uses a slightly modified version of Lawson and Hanson's nonlinear least-square solver method. Expectation values of the Hamiltonian of each molecule are determined for each θ value, at 114. The whole process can be repeated multiple times, as shown by the optimizer loop 112, to improve the precision of this approach and to converge as closely as possible to the solution θ* that is acceptable for chemical accuracy, at 116.

As stated above, it must be appreciated that an accurate representation of a molecule's Hamiltonian using atomic orbitals, requires as many qubits as the number of atomic orbitals, which is also subject to change, using different basis sets to express the molecule, e.g. STO-3G, 6-31G, etc. STO-3G are a type of basis sets using n-primitive Gaussian orbitals that are filled to Slater-type orbital (STO). For example, an STO-3G basis set for the 1s, 2s and 2p orbital of the carbon atom are all linear combination of three primitive Gaussian functions such that $\psi_{STO-3G} = c_1\phi_1 + c_2\phi_2 + c_3\phi_3$. 6-31G is another conventional type of basis set using Gaussian functions.

As stated in the above paragraphs, if the number of qubits allotted is equal to the number of atomic orbitals required for accurate modelling, no action or transformation is required on the Hamiltonian structure. If the number of qubits allotted is greater than the number of atomic orbitals required for accurate modelling, the number of qubits would cause a mismatch between the two objects, because there would be a surplus in size in the circuit when comparing the ranks of the two components. To address this issue, the necessary space for the Hamiltonian is padded with zeros to match the shape of the circuit in order to maintain the same physical properties (i.e. eigenvalues).

Figure 4:
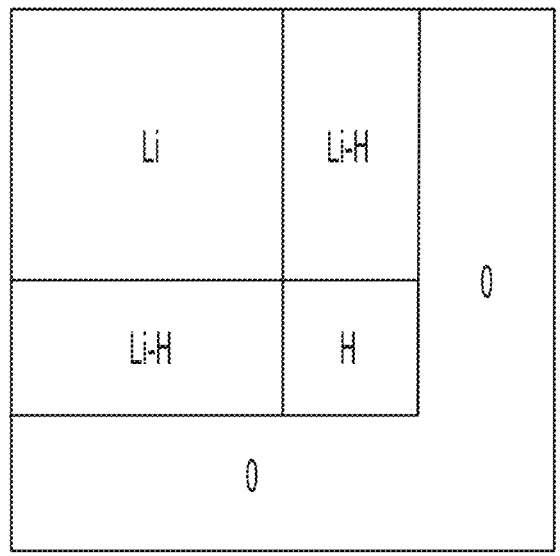
FIG. 4 is a visual representation showing the discrepancy between the Hamiltonian of LiH and the number of qubits used, according to an embodiment of the present disclosure.

FIG. 4 is a visual representation showing the discrepancy between the Hamiltonian of LiH and the number of qubits used, according to an embodiment of the present disclosure. For example, for the molecule LiH, which in the STO-3G basis, requires six atomic orbitals to be simulated. On the other hand, the circuit as designed has eight qubits allotted. Therefore, there is a difference in the ranks of the two Hamiltonian matrices associated with the qubits and the atomic orbitals. In this case, zeros are added to the rank transformation of the Hamiltonian matrix.

Figure 5:
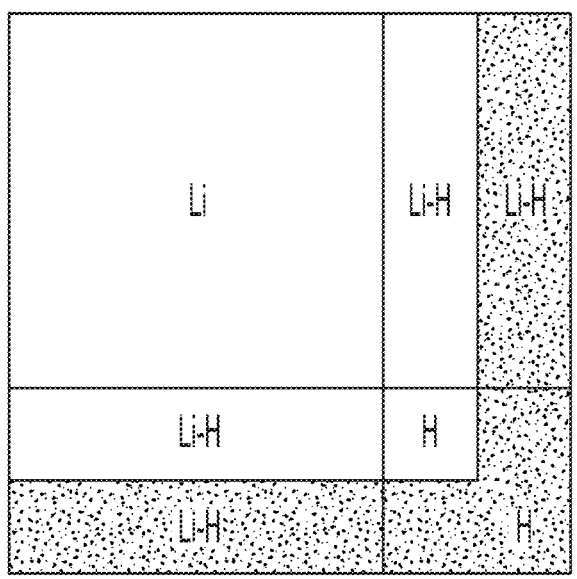
FIG. 5 is a visual representation showing the discrepancy between the Hamiltonian of LiH and the number of qubits used, according to another embodiment of the present invention.

If the number of qubits allotted is less than the number of atomic orbitals required for accurate modelling, the number of qubits is not sufficient for accurate modelling. In this case, in order to make the matrices describing the Hamiltonian and the circuit of equal rank, some atomic orbitals that would correspond to a higher number of qubits than the one specified are discarded. FIG. 5 is a visual representation showing the discrepancy between the Hamiltonian of LiH and the number of qubits used, according to another embodiment of the present invention. In this case, the initial Hamiltonian system has to discard some of its atomic orbitals (shaded in grey) in order to reduce its rank.

After constructing a single body integral coefficients in a matrix format, in order to give them physical meaning as a Hamiltonian, they undergo the Jordan-Wigner transformation wherein the appropriate operators act on the coefficients, with the resulting product being the construction of the desired Hamiltonian for each candidate molecule.

The minimization of the cost function is implemented with the application of two interweaving optimizations, one over the Euler angle θ that govern the expectation values of the Hamiltonian of each molecule, and another over the weights associated with the contribution to the sum of each Hamiltonian of the molecules.

In an embodiment, both optimization algorithms can be restricted into only a few iterations at a time instead of waiting for full convergence, in order for one to assist the other. In an embodiment, the algorithm selected for the optimization of the θ is L-BFGS-B, as it is found to be the most efficient one for a small amount of allowed iterations over other alternatives. In an embodiment, the algorithm selected for the optimization of the weight coefficients is Sequential Least Squares Programming (SLSQP), because it is the optimizer that allows the introduction of constraints on the optimization, such as $\Sigma c_i = 1$ with ease and specializes in the optimization of scalar variables such as the weights allocated to each candidate compound.

Figure 6:
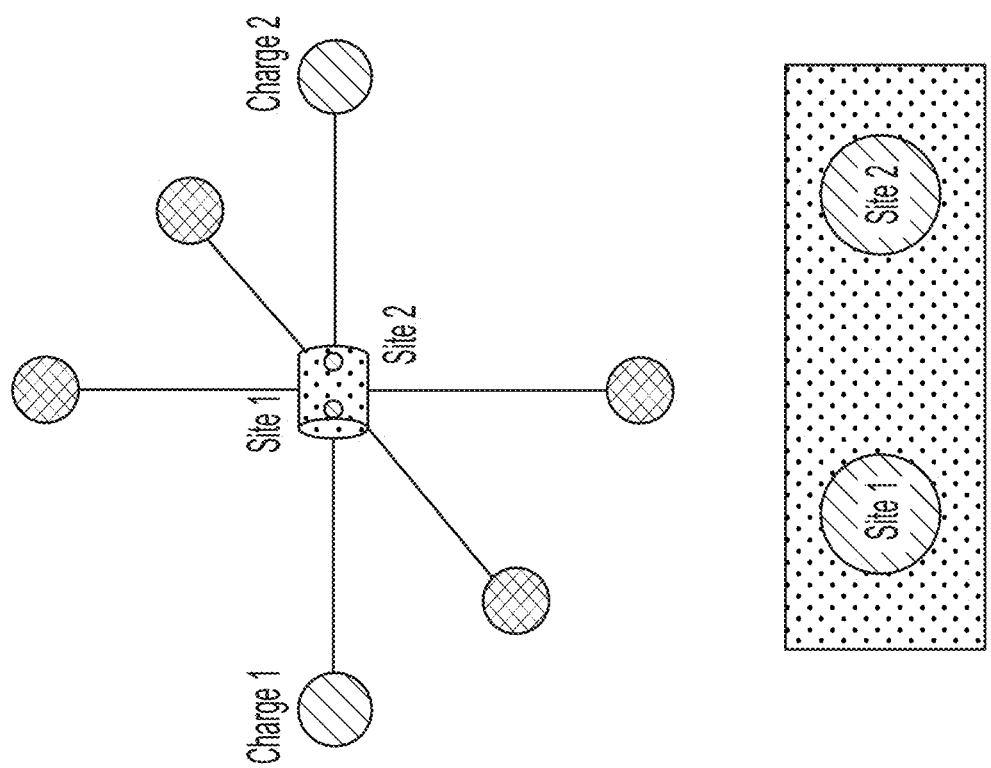
FIG. 6 is a schematic diagram illustrating a compound (molecule) in an environment of interest, according to an embodiment of the present invention.

FIG. 6 is a schematic diagram illustrating a compound (molecule) in an environment of interest, according to an embodiment of the present invention. The cylindrical shape with two dots represents the molecule, the spheres surrounding the molecule represent the environment. The two dots within the cylinder represents the atoms of the molecule placed at site 1 and site 2, respectively. The environment of interest can be simulated, for example, by placing charges at selected positions around the molecule. For example, as depicted in FIG. 6, the charges can be placed symmetrically with respect to the molecule. Control charges, i.e., charges that are varied, are placed symmetrically within an axis of the molecule. For example, the lowest energy configuration may correspond to the molecule represented by the cylindrical shape also oriented along the same axis where the control charges are located.

Figure 7:
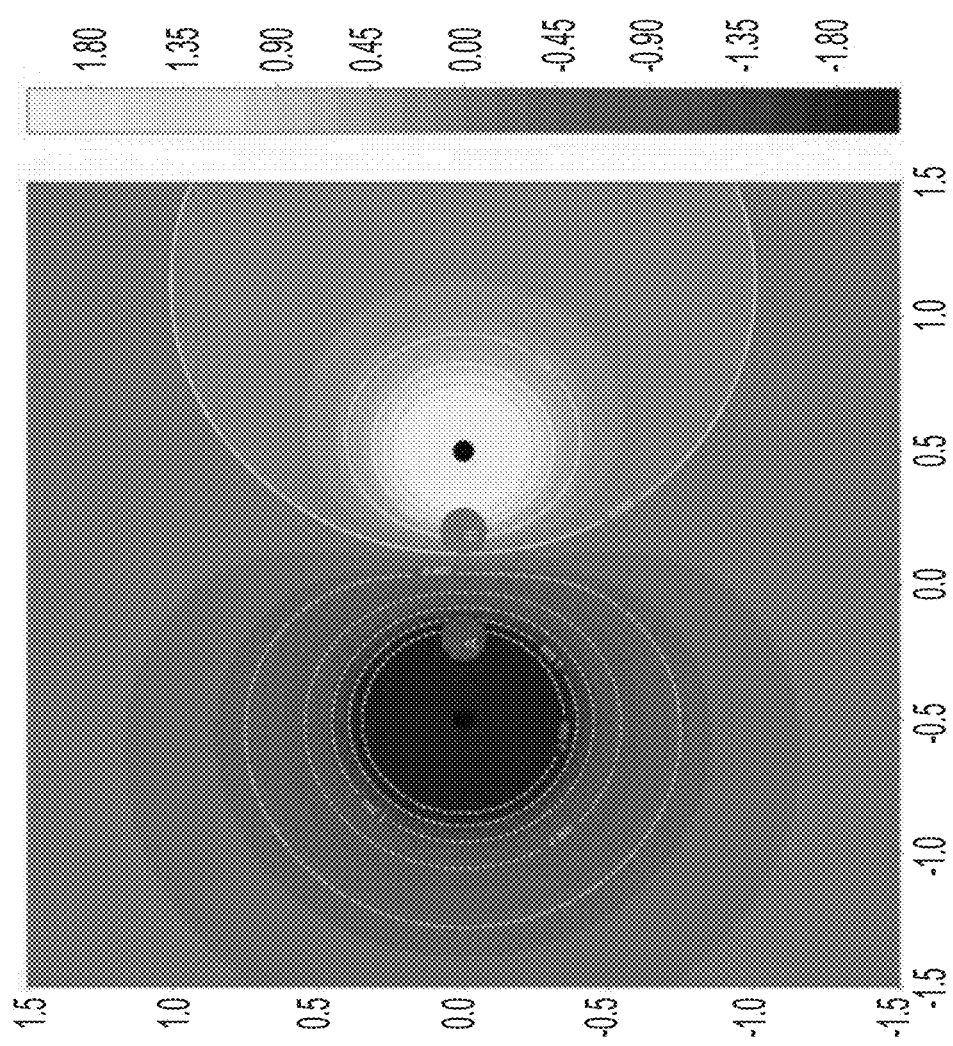
FIG. 7 is contour plot illustrating the electric field generated by the charges representing the environment of interest around the molecule, according to an embodiment of the present invention.

FIG. 7 is contour plot illustrating the electric field generated by the charges representing the environment of interest around the molecule, according to an embodiment of the present invention. The position of the atoms of the molecule AB (in the present example a diatomic molecule) is also shown in contour plot. The atoms of the molecules are represented by two spheres A and B. In this example, the environment of interest is simulated by two charges that are represented by two black dots in FIG. 7. The charges are aligned along the A-B bond of the diatomic molecule AB.

In the following paragraphs, we describe the application of the above described method for a specific molecular system example to illustrate the power of the present method in finding a best molecule for a specific environment. For example, in an embodiment, a linear combination or superposition of the following molecules ($Li_2$, LiH, HLi, NaH, HNa, and LiNa) is analyzed to extract the best molecule or molecules among this linear combination that best "fit" the environment of interest, i.e., the molecule having the lowest energy ground state in the environment of interest. In this example, the environment of interest is simulated by two point charges that create an electrical field around the molecule, as illustrated in FIG. 7. A superposition of all the molecules can be expressed as follows ⅙ ($Li_2$+LiH+HLi+NaH+HNa+LiNa). Initially, the plurality of molecular species in the linear superposition $Li_2$+LiH+NaH+HNa+LiNa are initially weighted by equal initial coefficients, in this case ⅙, as there are 6 molecular species, as described in the method at S10 of FIG. 1.

Initially, the system is run through the method with no charges around it, both the ambient and the control charges are set to zero. This gives a first impression of how each combination of elements reacts at gas phase, as in, not perturbed by any external potential. In an embodiment, the position of the candidates for each position is set, for example, to +1.175/-1.175 (atomic unit) of the Z axis. The results of the computation applying the method using a quantum computer are plotted to show the relative probability coefficient of each molecular specie in the linear superposition of molecular species.

Figure 8:
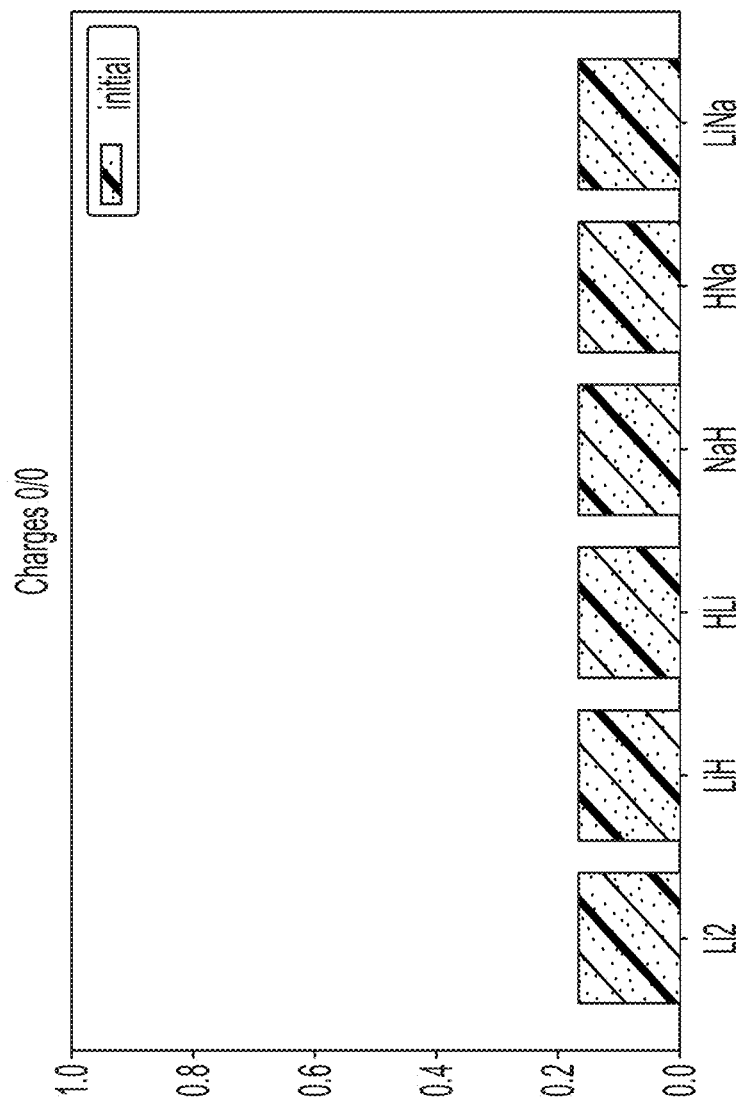
FIG. 8 is a bar graph showing initial probabilities or coefficients of each molecule in the linear combination of molecules for being selected as the best molecule in a specific environment, in this case vacuum environment, according to an embodiment of the present invention.

FIG. 8 is a bar graph showing initial probabilities or coefficients of each molecule in the linear combination of molecules for being selected as the best molecule in a specific environment, in this case vacuum environment, according to an embodiment of the present invention. As shown FIG. 8, initially, for a vacuum environment where no charges are placed around the molecule, each molecule in the linear combination ($Li_2$, LiH, HLi, NaH, HNa, LiNa) is set as having equal probability of having the lowest energy ground state. This corresponds to the initialization of the method.

Figure 9:
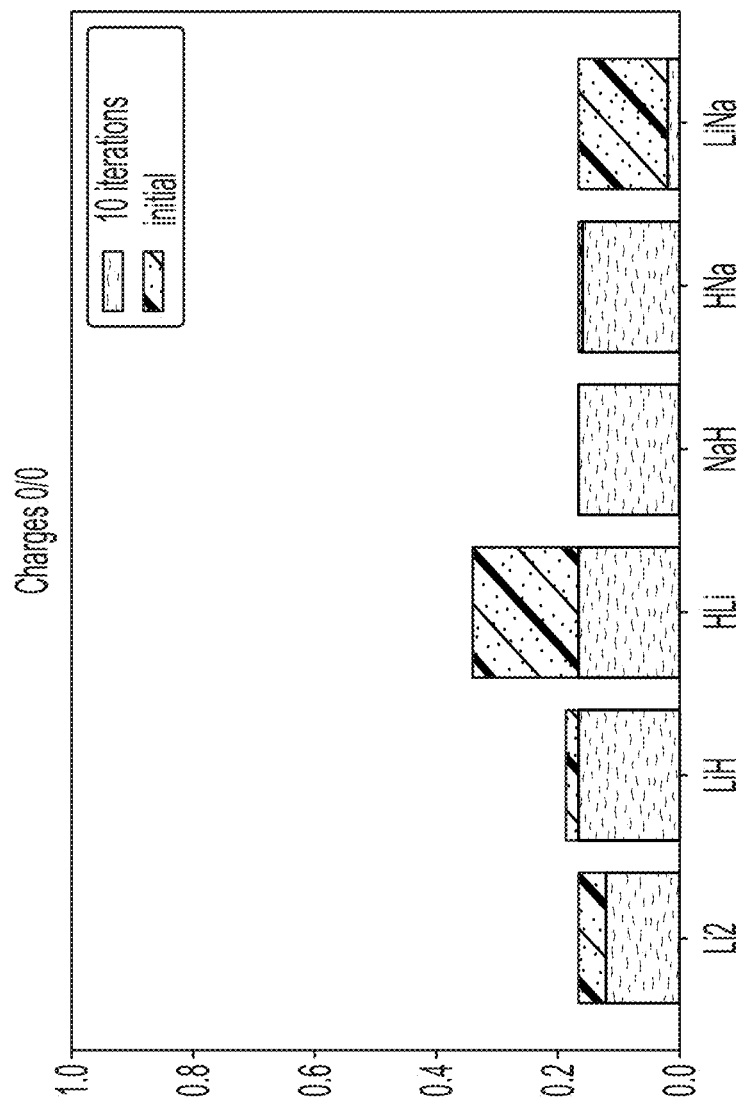
FIG. 9 is a bar graph showing probabilities or coefficients of each molecule in the linear combination of molecules for being selected as the best molecule in a vacuum environment, after ten iterations of the method, according to an embodiment of the present invention.

FIG. 9 is a bar graph showing probabilities or coefficients of each molecule in the linear combination of molecules for being selected as the best molecule in a vacuum environment, after ten iterations of the method, according to an embodiment of the present invention. As shown in FIG. 9, for a vacuum environment where no charges are placed around the molecule, after 10 iterations, the probability of each of the molecules in the linear combination ($Li_2$, LiH, HLi, NaH, HNa, LiNa) changes. As shown in FIG. 9, after ten iteration, the probability of having HLi as the molecule having the lowest ground energy state is higher that the probabilities of the other molecules. For example, the probability of having HLi as the molecule with the lowest energy ground state after 10 iterations increased relative to the initial probability (zero iteration) whereas the probability of having NaLi as the molecule with the lowest energy ground state after 10 iterations decreased relative to the initial probability (zero iteration).

Figure 10:
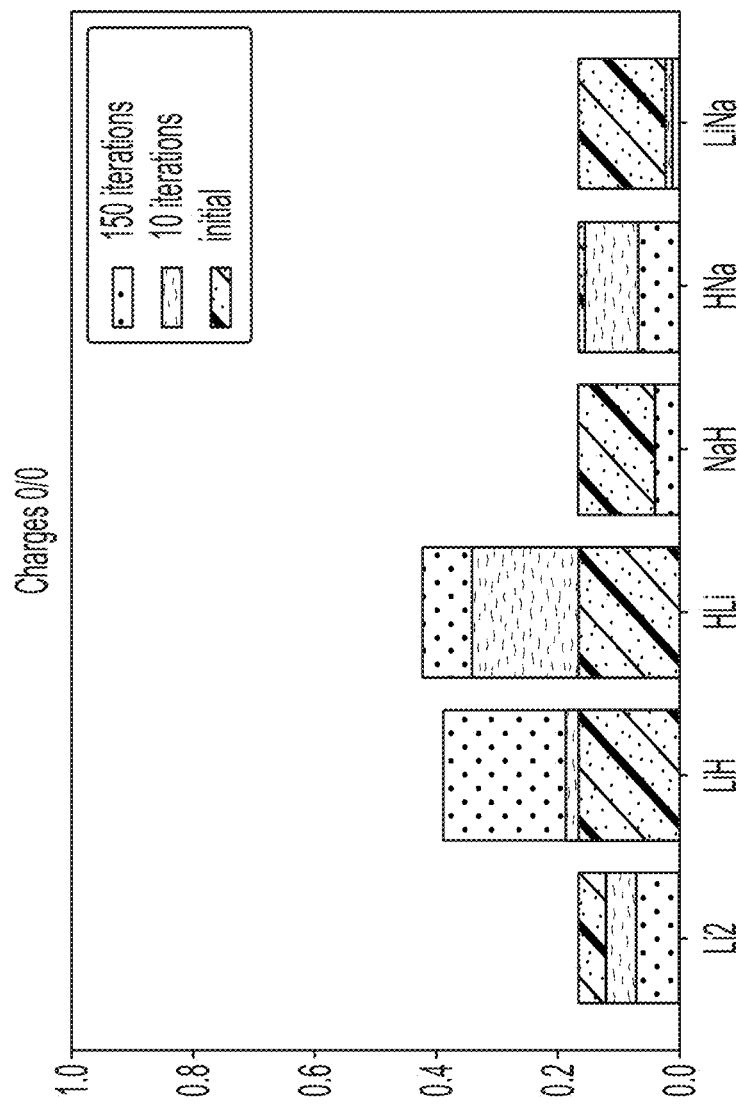
FIG. 10 is a bar graph showing probabilities or coefficients of each molecule in the linear combination of molecules for being selected as the best molecule in a vacuum environment, after 150 iterations, according to an embodiment of the present invention.

FIG. 10 is a bar graph showing probabilities or coefficients of each molecule in the linear combination of molecules for being selected as the best molecule in a vacuum environment, after 150 iterations, according to an embodiment of the present invention. As shown FIG. 10, for a vacuum environment where no charges are placed around the molecule, after 150 iterations, The probability of each of the molecules in the linear combination ($Li_2$, LiH, HLi, NaH, HNa, LiNa) changes. As shown in FIG. 9, after 150 iterations, the probability of having HLi as the molecule having the lowest ground energy state is higher than the probabilities of the other molecules and LiH appears to be a close second. For example, the probability of having HLi as the molecule with the lowest energy ground state after 150 iterations increased relative to initial probability (zero iteration) whereas the probability of having NaLi as the molecule with the lowest energy ground state after 150 iterations decreased relative to the initial probability (zero iteration).

Figure 11:
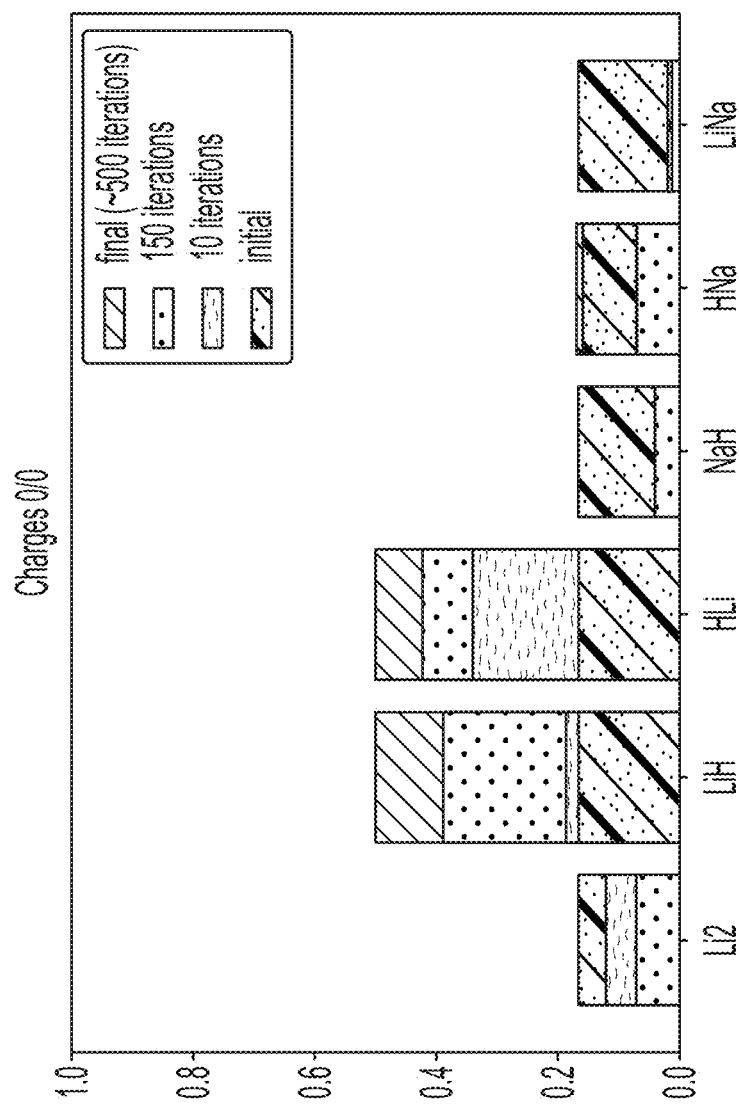
FIG. 11 is a bar graph showing probabilities or coefficients of each molecule in the linear combination of molecules for being selected as the best molecule in a vacuum environment, after 500 iterations, according to an embodiment of the present invention.

FIG. 11 is a bar graph showing probabilities or coefficients of each molecule in the linear combination of molecules for being selected as the best molecule in a vacuum environment, after 500 iterations, according to an embodiment of the present invention. As shown FIG. 11, for a vacuum environment where no charges are placed around the molecule, after 500 iterations, the probability of each of the molecules in the linear combination ($Li_2$, LiH, HLi, NaH, HNa, LiNa) changes. As shown in FIG. 11, after 500 iterations, the probability of having HLi or LiH as the molecule having the lowest ground energy state is higher than the probabilities of the other molecules. After 500 iterations, the probabilities of obtaining HLi becomes approximately equal to the probability of obtaining LiH as the molecule with the lowest energy ground state. This is an expected result as the molecule is symmetric in free space, in vacuum. In addition, the probability of having HLi or LiH as the molecule with the lowest energy ground state after 500 iterations increased further relative to the initial probability (zero iteration) whereas the probability of having NaLi as the molecule with the lowest energy ground state after 500 iterations decreased relative to the initial probability (zero iteration).

Figure 12A:
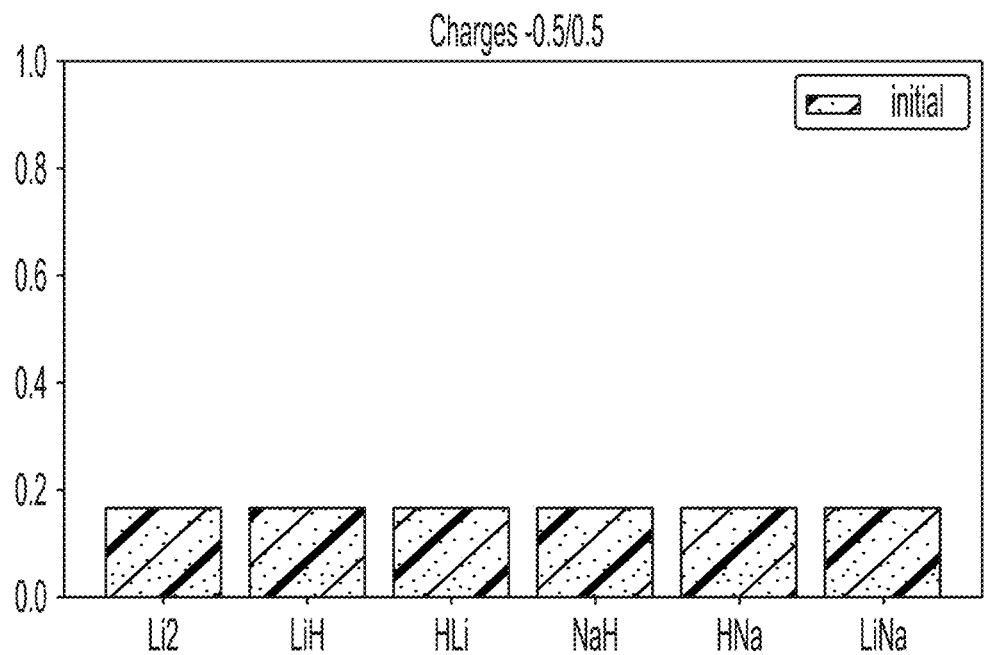
FIG. 12A is a bar graph showing initial probabilities of each molecule in the linear combination of molecules for being selected as the best molecule in the environment of interest, in this case in an environment where charges are placed at coordinates −0.5 and 0.5 along the axis of the molecule, according to an embodiment of the present invention.
Figure 12B:
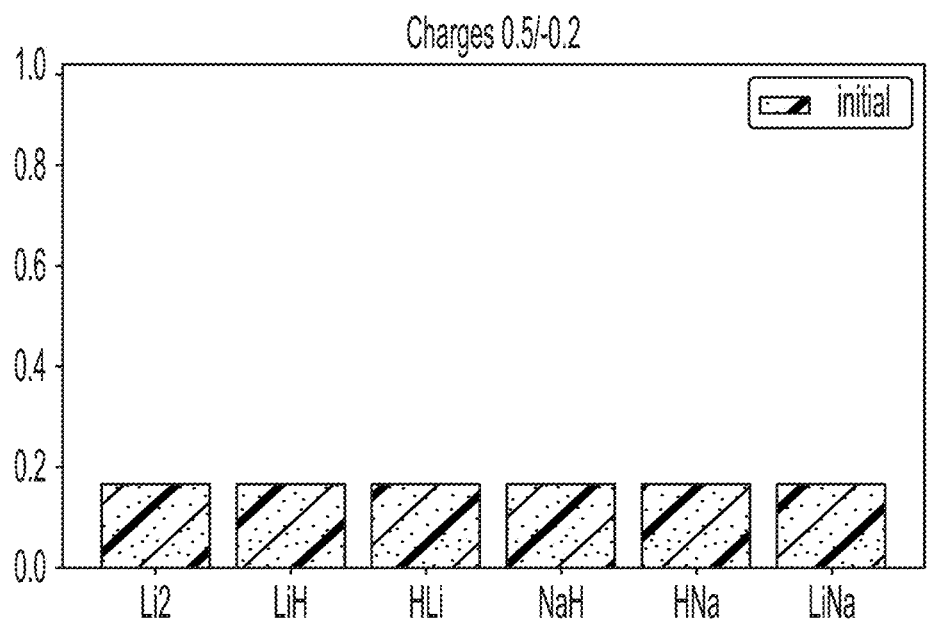
FIG. 12B is a bar graph showing initial probabilities of each molecule in the linear combination of molecules for being selected as the best molecule in an environment of interest, in this case in an environment where charges are placed at coordinates 0.5 and −0.2 along the axis of the molecule, according to an embodiment of the present invention.

FIG. 12A is a bar graph showing initial probabilities of each molecule in the linear combination of molecules for being selected as the best molecule in the environment of interest, in this case in an environment where charges are placed at coordinates −0.5 and 0.5 along the axis of the molecule, according to an embodiment of the present invention. FIG. 12B is a bar graph showing initial probabilities of each molecule in the linear combination of molecules for being selected as the best molecule in an environment of interest, in this case in an environment where charges are placed at coordinates 0.5 and −0.2 along the axis of the molecule, according to an embodiment of the present invention. Initially, each molecule in the linear combination ($Li_2$, LiH, HLi, NaH, HNa, LiNa) is set as having equal probability of having the lowest ground state. This corresponds to the initialization of the method, similar to the initialization shown in FIG. 8 (in vacuum).

Figure 13A:
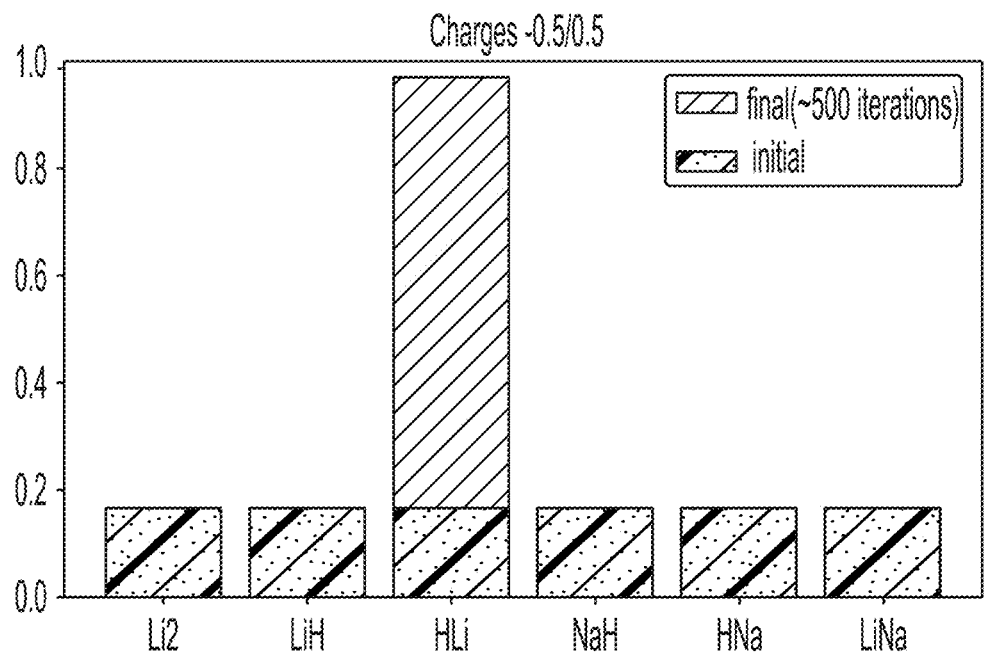
FIG. 13A is a bar graph showing probabilities of each molecule in the linear combination of molecules for being selected as the best molecule in the environment of interest, in this case in an environment where charges are placed at coordinates −0.5 and 0.5 along the axis of the molecule, after 500 iterations, according to an embodiment of the present invention.

FIG. 13A is a bar graph showing probabilities of each molecule in the linear combination of molecules for being selected as the best molecule in the environment of interest, in this case in an environment where charges are placed at coordinates −0.5 and 0.5 along the axis of the molecule, after 500 iterations, according to an embodiment of the present invention. As shown FIG. 13A, for the environment where charges are placed at −0.5 and 0.5 along the axis of the molecule, after 500 iterations, the probability of each of the molecules in the linear combination ($Li_2$, LiH, HLi, NaH, HNa, LiNa) changes. As shown in FIG. 13A, after 500 iterations, the probability of having HLi as the molecule having the lowest ground energy state is higher than the probabilities of the other molecules having the lowest energy ground state, including LiH. It is noted that contrary to the vacuum environment, in this case where charges are placed in the environment of the molecule, the probability of having the HLi as the molecule with the lowest energy ground state is approximately 1 and is greater than the probability of obtained its symmetrical molecule LiH with the lowest energy ground state.

Figure 13B:
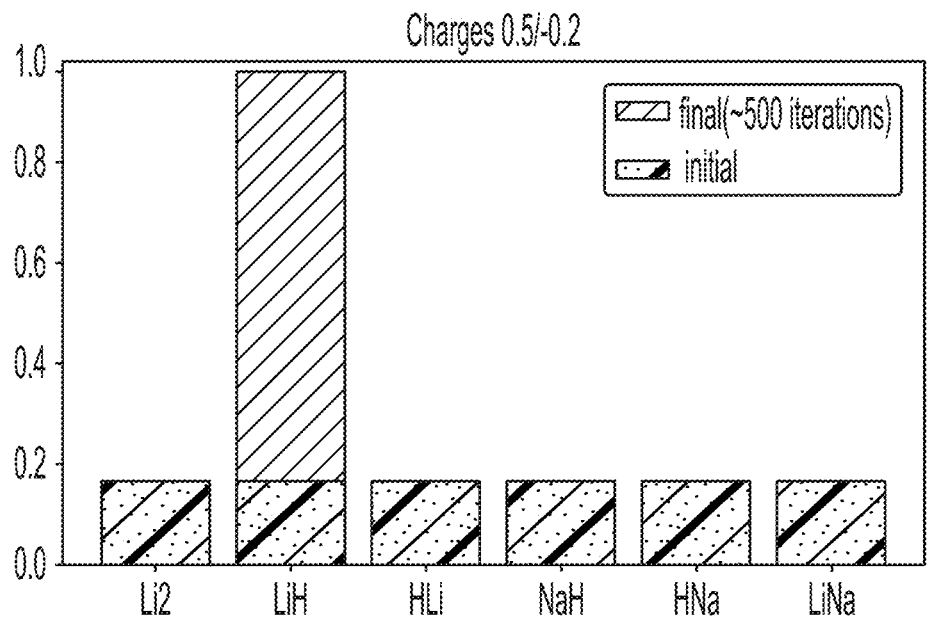
FIG. 13B is a bar graph showing probabilities of each molecule in the linear combination of molecules for being selected as the best molecule in the environment of interest, in this case in an environment where charges are placed at coordinates 0.5 and −0.2 along the axis of the molecule, after 500 iterations, according to an embodiment of the present invention.

FIG. 13B is a bar graph showing probabilities of each molecule in the linear combination of molecules for being selected as the best molecule in the environment of interest, in this case in an environment where charges are placed at coordinates 0.5 and −0.2 along the axis of the molecule, after 500 iterations, according to an embodiment of the present invention. As shown FIG. 13B, for the environment where charges are placed 0.5 and −0.2 along the axis of the molecule, after 500 iterations, the probability of each of the molecules in the linear combination ($Li_2$, LiH, HLi, NaH, HNa, LiNa) changes. As shown in FIG. 13B, after 500 iterations, the probability of having LiH as the molecule having the lowest ground energy state is higher than the probabilities of the other molecules having the lowest energy ground state, including HLi. It is noted that contrary to the vacuum environment, in this case where charges are placed in the environment of the molecule, the probability of having the LiH as the molecule with the lowest energy ground state is approximately 1 and is greater than the probability of obtaining its symmetrical molecule HLi with the lowest energy ground state. It is also noted that upon changing the placement of the charges from −0.5/0.5 to 0.5/−0.2, the molecule selected as having the lowest energy ground state changes from HLi to LiH which can be explained by the dipole moment of the molecule. Indeed, LiH can be seen as having the dipole moment $Li^-H^+$ and HLi can be seen as having the dipole moment $H^+Li^-$. Consequently, placing the charges at −0.5/+0.5 would favor the dipole moment orientation $H^+Li^-$, i.e., HLi, whereas placing the charges at +0.5/−0.2 would favor the dipole moment orientation $Li^+H^+$, i.e., LiH.

Figure 14A:
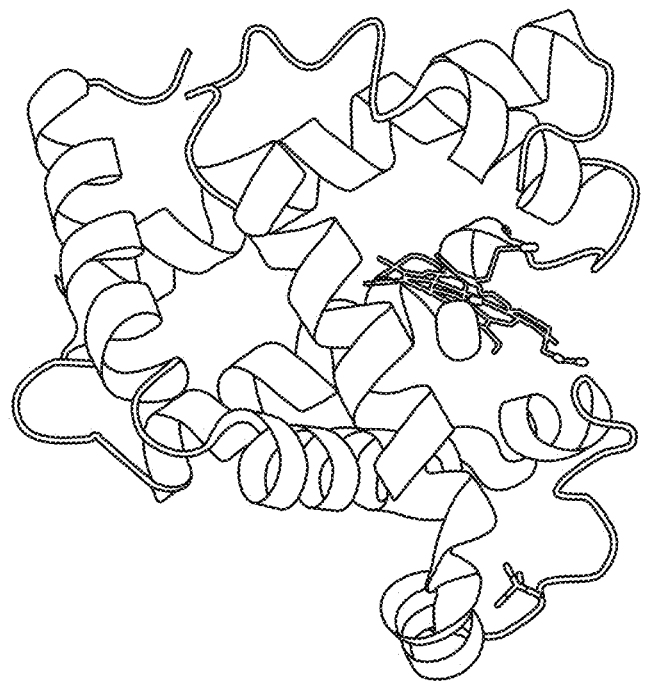
FIG. 14A shows a three-dimensional molecular configuration of the myoglobin (Mb) protein that creates an environment in which a complex molecular system interacts with the environment, according to an embodiment of the present invention.
Figure 14B:
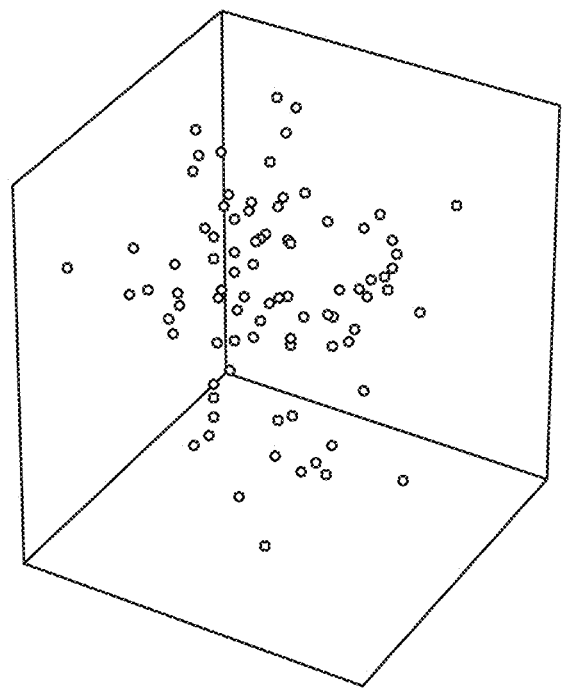
FIG. 14B is a schematic representation of a distribution of protein charges from the Mb molecule in space, according to an embodiment of the present invention. The method can optimize the chemical nature of a binding molecule so as to minimize the interaction energy with the point charges of the Mb protein.

Although, the method of the present invention is illustrated above as being applied to a diatomic molecule, as it must be appreciated, the method of the present invention can be applied to a more complex molecular systems. FIG. 14A shows a three-dimensional molecular configuration of the myoglobin (Mb) protein that creates an environment in which a complex molecular system interacts with the environment, according to an embodiment of the present invention. Myoglobin (Mb) protein is an iron-binding and oxygen-binding protein found in the muscle tissue of vertebrates in general and in almost all mammals. The protein can be simulated as protein charges. FIG. 14B is a schematic representation of a distribution of protein charges from the Mb molecule in space, according to an embodiment of the present invention. The method can optimize the chemical nature of a binding molecule so as to minimize the interaction energy with the point charges of the Mb protein.

In the following paragraphs we will explain the combinatorial aspect of the method. If the set $\{1, \ldots, N_P\}$ is the number of possible positions, and $\{1, \ldots, N_A\}$ the number of possible atoms/elements that can be used at a position, it can be shown that the Hamiltonian that is needed to be calculated scales quadratically $O(N_A^2 N_P^2)$ and the order of the problem is $O(N_P N_A)$, instead of running into a combinatorial explosion of $O(N_P^{N_A})$ where a full enumeration of the possible combination is required. If we assume an $a_{jk}$ which is a fraction of j at the position k, with $$1 \leq j \leq N_A \qquad (16)$$

$$1 \leq k \leq N_P \qquad (17)$$

so that j is an index that describes Positions and k is an index that describes atoms. For $\forall k: \Sigma_{j=1}^{N_A} a_{jk}=1$ means that each given position we can only have a sum of one atom. In other words, it denotes the relaxation from a discrete problem to a continuous problem.

From a chemical standpoint, this transition does not make sense initially, as the problem is at first well defined and at a continuous set would mean there could be "half atoms" whereas in discrete format we only get one atom/element per position. From a mathematical standpoint, this transition is done in order to be able to exploit sampling techniques in a histogram instead of just enumerating all the possible combinations in the problem. In a more comprehensive manner of expression, the various interactions can be written as a Nucleus-Nucleus interaction, a Nucleus-Electron interaction, and an electron-electron interaction, as follows.

Nucleus-Nucleus interaction:

$$\sum_{\substack{i<j \\ k<l}} \frac{Z_i(R_k)Z_j(R_l)}{|R_k - R_l|} \quad (18)$$

In this way, the energy of the Nucleus-Nucleus interaction can be written as $$E_{NN} = \langle\psi(r)|H_{NN}|\psi(r)\rangle = \langle\psi|\psi\rangle H_{NN} = \sum_{\substack{i<j \\ k<l}} a_\mu a_\nu \frac{Z_i(R_k)Z_j(R_l)}{|R_k - R_l|} \quad (19)$$

Nucleus-Electron interaction: Expressing the system in the second quantization: $\mu=(ik)$ and $\nu=(jl)$ where $i, j \in N_A$ and $k, l \in N_P$ $$\sum_{\mu,\nu} a_\mu a_\nu h_{\mu\nu} \alpha_\mu^\dagger \alpha_{nu} = f(a) \quad (20)$$

where $$h_{\mu\nu} = \langle\phi_\mu(r)|V_{Nucleus \to el}(r)|\phi_\nu(r)\rangle \quad (21)$$

$$V_{Nucleus \to el}(r) = -\sum_{i=1}^{N_A}\sum_{k=1}^{N_P}\left(\frac{Z_i(R_k)}{|R_k - r|} + u_{ECP}^{i,k}(r - R_k)\right) \quad (22)$$

and $\phi_\mu$ is an atomic orbital associated to atom i in position k. The total wavefunction would be:

$$|\omega(r_1, \ldots, r_N)\rangle = |\phi_{11}(r_1) \ldots \phi_{N_A N_P}(r_N)\rangle \quad (23)$$

Electron-Electron interaction: The electron-electron interaction is also written in the form of second quantization, wherein $$h_{\alpha\beta\gamma\delta} = \left\langle\phi_\alpha(r_1)\phi_\beta(r_2)\left|\frac{1}{r_1 - r_2}\right|\phi_\gamma(r_1)\phi_\delta(r_2)\right\rangle \quad (24)$$

with $\alpha = i_1 k_1, \beta = i_2 k_2, \gamma = i_3 k_3, \delta = i_4 k_4$

We arrive at the conclusion that f(a) is a well-defined function whose continuous solution can be mapped back to the original problem and regain its chemical meaning. Continuous solutions have chemical meaning in the respect that each Hamiltonian describing a chemical pair is weighted with a coefficient a, whose minimized such as only one of the $a_i$ to have a value of 1 and the rest a value of 0.

Finally, the cost function for evaluation can be written in the form of:

$$\min_{a,\theta}\langle\omega(\theta)|H(a, \theta, R)|\omega(\theta)\rangle + \lambda\|a\|_1 \quad (25)$$

where $\lambda\|a\|_1$ is called a lasso and is used for optimization purposes. The parameter $\lambda>0$ can help reduce a number of non-zero components in $\alpha$.

In some embodiments, programs for performing the methods in accordance with embodiments of the invention can be embodied as program products in a computer such as a personal computer or server or in a distributed computing environment comprising a plurality of computers that interacts with a quantum computer by sending instructions to and receiving data from the quantum computer. The personal computer may include, for example, a desktop computer, a laptop computer, a handheld computing device such as a PDA, a tablet, etc. The computer program products may include a computer readable medium or storage medium or media having instructions stored thereon used to program the quantum computer to perform the methods described above. Examples of suitable storage medium or media include any type of disk including floppy disks, optical disks, DVDs, CD ROMs, magnetic optical disks, RAMs, EPROMs, EEPROMs, magnetic or optical cards, hard disk, flash card (e.g., a USB flash card), PCMCIA memory card, smart card, or other media. Alternatively, a portion or the whole computer program product can be downloaded from a remote computer or server via a network such as the internet, an ATM network, a wide area network (WAN) or a local area network.

Stored on one or more of the computer readable media, the program may include software for controlling both the hardware of a general purpose or specialized computer or processor. The software also enables the computer or processor to interact with a quantum computer to send instructions to the quantum computer and read outputs from the quantum computer.

Figure 15:
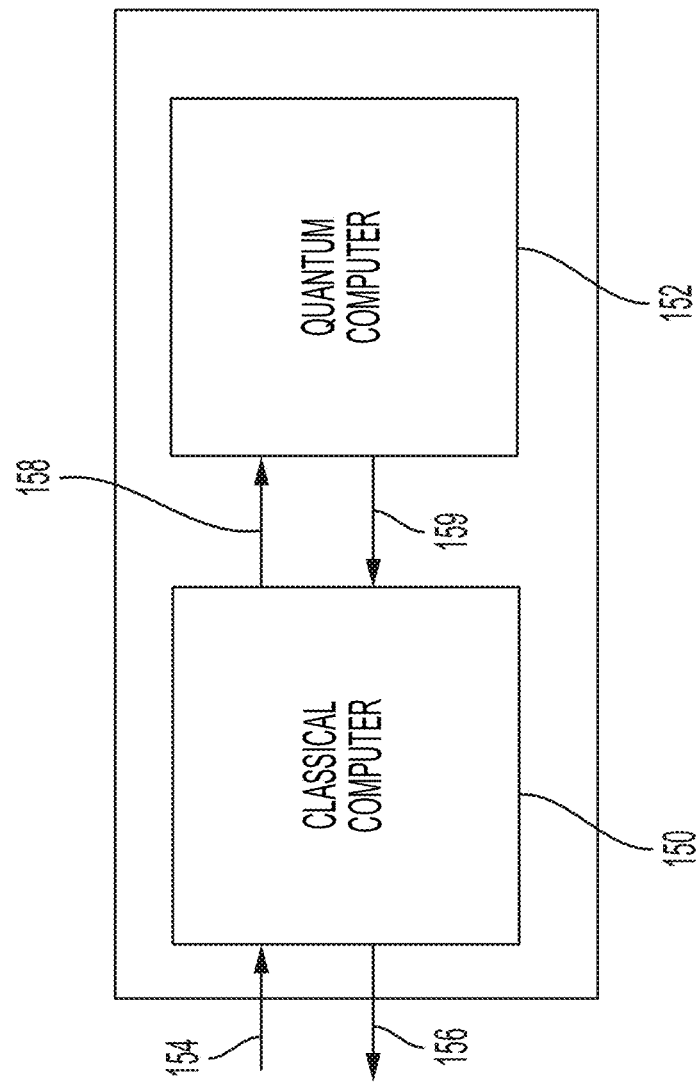
FIG. 15 is a schematic diagram illustrating the interaction between a classical computer and a quantum computer for implementing the method, according to an embodiment of the present invention.

FIG. 15 is a schematic diagram illustrating the interaction between a classical computer and a quantum computer for implementing the method, according to an embodiment of the present invention. The classical computer 150 provides inputs and receives outputs from the quantum computer 152. The outputs may include results of a computation of the method described herein. In an embodiment, the classical computer 150 may receive inputs 154 from a user or other entity and returns outputs 156 to the user. The classical computer 150 can be programmed to input various parameters of a molecular system such as the linear combination of molecular species as specified by the user to the quantum computer 152 via input line 158. The classical computer 150 can be any type of conventional computer including, for example, a personal computer, a supercomputer, a server computer, a tablet, or any other handheld device including a smartphone. The classical computer 150 interfaces with the quantum computer 152 via quantum computer input 158 and quantum computer output 159. The classical computer 150 sends commands or instructions to the quantum computer 152 via input 158 and the quantum computer 152 returns outputs of a quantum computation to the classical computer 150 via output 159. The quantum computer 152 includes one or more quantum circuits having a plurality of qubits and operator gates, for example as shown and described above with respect to FIG. 3, for implementing the computation of the method described herein. In an embodiment, the quantum computer 152 is a superconducting quantum computer using superconducting Josephson junction qubits.

In an embodiment, the input 158 and output 159 (interface to the quantum computer 152) operate as digital to analog converters ((AC), and analog to digital converters (ADC). In an embodiment, the inputs and outputs (interface) 158 and 159 can be configured to minimize environmental effects on the quantum computer 152. For example, the input 158 and output 159 can he configured to isolate the quantum computer 152 from noise, temperature variation, undesirable signal couplings and other effects. The input 158 and output 159 can be configured to operate as serial or as parallel communication channels. The input 158 and output 159 can include semiconductor circuits, superconductor circuits, optical devices and channels, digital circuits, and analog circuits, etc.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

We claim:

1. A method of designing a molecule for an environment of interest using a quantum computer, comprising:
    providing a linear superposition of a plurality of molecular species, the plurality of molecular species in the linear superposition being initially weighted by equal initial coefficients;
    determining a lowest-energy quantum state for the superposition of the plurality of molecular species in a vacuum environment using a quantum optimization process on the quantum computer;
    determining a lowest-energy quantum state for the superposition of the plurality of molecular species in the environment of interest using the quantum optimization process on the quantum computer;
    calculating a difference in lowest energy states between the vacuum environment and the environment of interest for each molecular species of the plurality of molecular species to provide a cost of the superposition of the plurality of molecular species;
    performing a quantum optimization process on the quantum computer to determine a minimum cost for the superposition of the plurality of molecular species and determine updated coefficients weighting the plurality of molecular species; and
    identifying the molecule for the environment of interest based on a comparison of the updated coefficients, wherein the identifying the molecule comprises identifying the molecule for the environment of interest having, atom-by-atom, the greatest coefficient in the updated coefficients, at each atomic position.

2. The method according to claim 1, wherein the determining the lowest-energy quantum state for the superposition of the plurality of molecular species in the vacuum and in the environment of interest comprises using a Variational Quantum Eigensolver (VQE) method with a mapping of corresponding atomic orbital wavefunctions to qubits in the quantum computer.

3. The method according to claim 1, wherein performing the quantum optimization process on the quantum computer to determine the updated coefficients weighting the plurality of molecular species comprises using a Variational Quantum Eigensolver (VQE) method.

4. The method according to claim 1, wherein the determining the lowest-energy quantum state for the superposition of the plurality of molecular species in the environment of interest includes selecting a plurality of locations of each of the superposition of the plurality of molecular species in the environment of interest.

5. The method of claim 1, further comprising providing a representation of the environment of interest on the quantum computer to simulate a physical environment of interest.

6. The method of claim 5, wherein providing the representation of the environment of interest comprises simulating the environment using electric charges placed at appropriate positions relative to each of the plurality of molecular species.

7. A quantum computer system to design a molecule for an environment of interest, the quantum computer system configured to:
    receive as input a linear superposition of a plurality of molecular species, the plurality of molecular species in the linear superposition being initially weighted by equal initial coefficients;
    determine a lowest-energy quantum state for the superposition of the plurality of molecular species in a vacuum environment using a quantum optimization process;
    determine a lowest-energy quantum state for the superposition of the plurality of molecular species in the environment of interest using the quantum optimization process;
    calculate a difference in lowest energy states between the vacuum environment and the environment of interest for each molecular species of the plurality of molecular species to provide a cost of the superposition of the plurality of molecular species;
    perform a quantum optimization process on the quantum computer to determine a minimum cost for the superposition of the plurality of molecular species and determine updated coefficients weighting the plurality of molecular species; and
    identify the molecule for the environment of interest based on a comparison of the updated coefficients, wherein the quantum computer system is configured to identify the molecule for the environment of interest having, atom-by-atom, the greatest coefficient in the updated coefficients, at each atomic position.

8. The quantum computer system according to claim 7, wherein the quantum computer system is configured to determine the lowest-energy quantum state for the superposition of the plurality of molecular species in the vacuum and in the environment of interest by using a Variational Quantum Eigensolver (VQE) method with a mapping of corresponding atomic orbital wavefunctions to qubits in the quantum computer system.

9. The quantum computer system according to claim 7, wherein the quantum computer system is configured to perform the quantum optimization process to determine the updated coefficients weighting the plurality of molecular species by using a Variational Quantum Eigensolver (VQE) method.

10. The quantum computer system according to claim 7, wherein the quantum computer system is configured to determine the lowest-energy quantum state for the superposition of the plurality of molecular species in the environment of interest by selecting a plurality of locations of each of the superposition of the plurality of molecular species in the environment of interest.

11. The quantum computer system according to claim 7, wherein the quantum computer system is configured to provide a representation of the environment of interest by simulating a physical environment of interest.

12. The quantum computer system according to claim 11, wherein the quantum computer system is configured to provide the representation of the environment of interest by simulating the environment using electric charges placed at appropriate positions relative to each of the plurality of molecular species.

13. A non-transitory computer readable medium on which is stored a program, which when executed by a quantum computer causes the quantum computer to:

receive as input a linear superposition of a plurality of molecular species, the plurality of molecular species in the linear superposition being initially weighted by equal initial coefficients;

determine a lowest-energy quantum state for the superposition of the plurality of molecular species in a vacuum environment using a quantum optimization process;

determine a lowest-energy quantum state for the superposition of the plurality of molecular species in the environment of interest using the quantum optimization process;

calculate a difference in lowest energy states between the vacuum environment and the environment of interest for each molecular species of the plurality of molecular species to provide a cost of the superposition of the plurality of molecular species;

perform a quantum optimization process on the quantum computer to determine a minimum cost for the superposition of the plurality of molecular species and determine updated coefficients weighting the plurality of molecular species;

identify the molecule for the environment of interest based on a comparison of the updated coefficients; and identify the molecule for the environment of interest having, atom-by-atom, the greatest coefficient in the updated coefficients, at each atomic position.

14. The non-transitory computer readable medium according to claim 13, wherein the program stored thereon, when executed by the quantum computer, causes the quantum computer to determine the lowest-energy quantum state for the superposition of the plurality of molecular species in the vacuum and in the environment of interest by using a Variational Quantum Eigensolver (VQE) method with a mapping of corresponding atomic orbital wavefunctions to qubits in the quantum computer system.

15. The non-transitory computer readable medium according to claim 13, wherein the program stored thereon, when executed by the quantum computer, causes the quantum computer to perform the quantum optimization process to determine the updated coefficients weighting the plurality of molecular species by using a Variational Quantum Eigensolver (VQE) method.

16. The non-transitory computer readable medium according to claim 13, wherein the program stored thereon, when executed by the quantum computer, causes the quantum computer to determine the lowest-energy quantum state for the superposition of the plurality of molecular species in the environment of interest by selecting a plurality of locations of each of the superposition of the plurality of molecular species in the environment of interest.

17. The non-transitory computer readable medium according to claim 13, wherein the program stored thereon, when executed by the quantum computer, causes the quantum computer to provide a representation of the environment of interest by simulating a physical environment of interest.

18. The non-transitory computer readable medium according to claim 17, wherein the program stored thereon, when executed by the quantum computer, causes the quantum computer to provide the representation of the environment of interest by simulating the environment using electric charges placed at appropriate positions relative to each of the plurality of molecular species.

* * * * *